United States Patent
Samset

(10) Patent No.: US 10,918,357 B2
(45) Date of Patent: Feb. 16, 2021

(54) METHODS AND SYSTEMS FOR AUTOMATICALLY DETERMINING AN ANATOMICAL MEASUREMENT OF ULTRASOUND IMAGES

(71) Applicant: General Electric Company, Schenectady, NY (US)

(72) Inventor: Eigil Samset, Oslo (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 673 days.

(21) Appl. No.: 15/639,887

(22) Filed: Jun. 30, 2017

(65) Prior Publication Data
US 2019/0000424 A1    Jan. 3, 2019

(51) Int. Cl.
*A61B 8/08* (2006.01)
*A61B 8/00* (2006.01)
*A61B 5/107* (2006.01)

(52) U.S. Cl.
CPC ............ *A61B 8/5223* (2013.01); *A61B 8/085* (2013.01); *A61B 8/0808* (2013.01); *A61B 8/0866* (2013.01); *A61B 8/0883* (2013.01); *A61B 8/0891* (2013.01); *A61B 8/463* (2013.01); *A61B 8/467* (2013.01); *A61B 8/5292* (2013.01); *A61B 8/54* (2013.01); *A61B 5/107* (2013.01); *A61B 8/469* (2013.01)

(58) Field of Classification Search
CPC ..... A61B 8/5223; A61B 8/085; A61B 8/0891; A61B 8/0883; A61B 8/0866; A61B 8/0808; A61B 8/5292; A61B 8/54; A61B 8/467; A61B 8/463; A61B 8/469; A61B 5/107; A61B 8/5215; A61B 8/48; A61B 8/461

See application file for complete search history.

(56) References Cited

U.S. PATENT DOCUMENTS

| | | | | |
|---|---|---|---|---|
| 5,588,435 A * | 12/1996 | Weng | ............ | A61B 8/0866 600/443 |
| 5,605,155 A * | 2/1997 | Chalana | ............ | A61B 5/1075 600/443 |
| 6,258,033 B1 * | 7/2001 | Grenon | ............ | A61B 8/06 600/458 |
| 6,561,980 B1 * | 5/2003 | Gheng | ............ | A61B 8/12 600/443 |
| 6,733,454 B1 * | 5/2004 | Bakircioglu | ............ | A61B 8/06 600/453 |
| 7,563,229 B2 * | 7/2009 | Heimdal | ............ | A61B 8/08 600/437 |

(Continued)

*Primary Examiner* — Sanjay Cattungal
(74) *Attorney, Agent, or Firm* — The Small Patent Law Group LLC; Dean D. Small

(57) ABSTRACT

The systems and methods described herein generally relate to automatically determining an anatomical measurement of an ultrasound image. The systems and methods identify a view characteristic of an ultrasound image. The ultrasound image including one or more anatomical features. The systems and methods select a diagnostic measurement (DM) tool based on the view characteristic, on a graphical user interface (GUI), which is generated on a display. The systems and methods receive a first selection at a first position within the ultrasound image, and automatically determine an anatomical measurement, to be performed upon the ultrasound image utilizing the DM tool, based on the first position.

22 Claims, 4 Drawing Sheets

(56) References Cited

U.S. PATENT DOCUMENTS

| | | | |
|---|---|---|---|
| 8,840,557 B2* | 9/2014 | Casciaro | A61B 8/4209 600/443 |
| 2002/0102023 A1* | 8/2002 | Yamauchi | G06F 19/00 382/199 |
| 2006/0064016 A1* | 3/2006 | Demi | A61B 8/14 600/450 |
| 2006/0173317 A1* | 8/2006 | Lee | A61B 8/0883 600/437 |
| 2009/0093717 A1* | 4/2009 | Carneiro | A61B 8/0866 600/443 |
| 2013/0281855 A1* | 10/2013 | Baba | A61B 8/5207 600/441 |
| 2015/0238148 A1 | 8/2015 | Georgescu | |
| 2016/0051232 A1* | 2/2016 | Yoo | A61B 8/468 600/440 |
| 2016/0058422 A1* | 3/2016 | Lee | G06T 7/62 600/443 |
| 2016/0081663 A1* | 3/2016 | Chen | A61B 8/085 600/425 |
| 2016/0100824 A1* | 4/2016 | Kim | G06F 19/321 600/437 |
| 2017/0007161 A1* | 1/2017 | Zou | A61B 5/1075 |
| 2018/0085043 A1* | 3/2018 | Panicker | A61B 8/485 |

* cited by examiner

METHODS AND SYSTEMS FOR AUTOMATICALLY DETERMINING AN ANATOMICAL MEASUREMENT OF ULTRASOUND IMAGES

FIELD

Embodiments described herein generally relate to automatically determining an anatomical measurement of an ultrasound image.

BACKGROUND OF THE INVENTION

During an ultrasound exam a series of ultrasound images (e.g., over fifty images) are acquired. The clinician (e.g., sonographer, doctor, nurse) performs a multiple anatomical measurements on the ultrasound images. To perform the anatomical measurements, the clinician must make several selections or clicks on a console of a conventional ultrasound imaging system. For example, the user selects a type of anatomical measurement to be performed. Based on the type of anatomical measurement, the ultrasound imaging system provides an appropriate measurement tool. The clinician performs the anatomical measurement by selecting and positioning the measurement tools on the ultrasound image. The described selections needed by the clinician to perform the anatomical measurements reduces the productivity of the ultrasound exam. The reduction in the productivity further increases a length of the ultrasound exam for the patient.

BRIEF DESCRIPTION OF THE INVENTION

In an embodiment, a method (e.g., method for automatically determine an anatomical measurement) is provided. The method includes identifying a view characteristic of an ultrasound image. The ultrasound image including one or more anatomical features. The method includes selecting a diagnostic measurement (DM) tool based on the view characteristic, on a graphical user interface (GUI), which is generated on a display. The method includes receiving a first selection at a first position within the ultrasound image, and automatically determining an anatomical measurement, to be performed upon the ultrasound image utilizing the DM tool, based on the first position.

In an embodiment, a system (e.g., a medical imaging system) is provided. The system includes an ultrasound probe configured to acquire ultrasound data of an anatomical structure, and a display. The system includes a controller circuit. The controller circuit is configured to select a diagnostic measurement (DM) tool based on the view characteristic, on a graphical user interface (GUI), which is generated on the display. The controller circuit is configured to receive a first selection at a first position within the ultrasound image, and automatically determine an anatomical measurement, to be performed upon the ultrasound image utilizing the DM tool, based on the first position.

In an embodiment, a method (e.g., method for automatically determine an anatomical measurement) is provided. The method includes identifying a view characteristic of an ultrasound image. The ultrasound imaging including one or more anatomical features. The method includes selecting a diagnostic measurement (DM) tool based on the view characteristic, on a graphical user interface (GUI). The DM tool has an associated set of contextual indicators that correspond to different types of anatomical measurements. The method includes receiving a first selection at a first position within the ultrasound image, and a second selection at a second position within the ultrasound image. The method includes identifying a select contextual indicator indicating a type of anatomical measurement to be obtained from the first and second selections, and automatically determining an anatomical measurement, to be performed upon the ultrasound image utilizing the DM tool, based on the first and second positions.

DETAILED DESCRIPTION OF THE INVENTION

Figure 1:
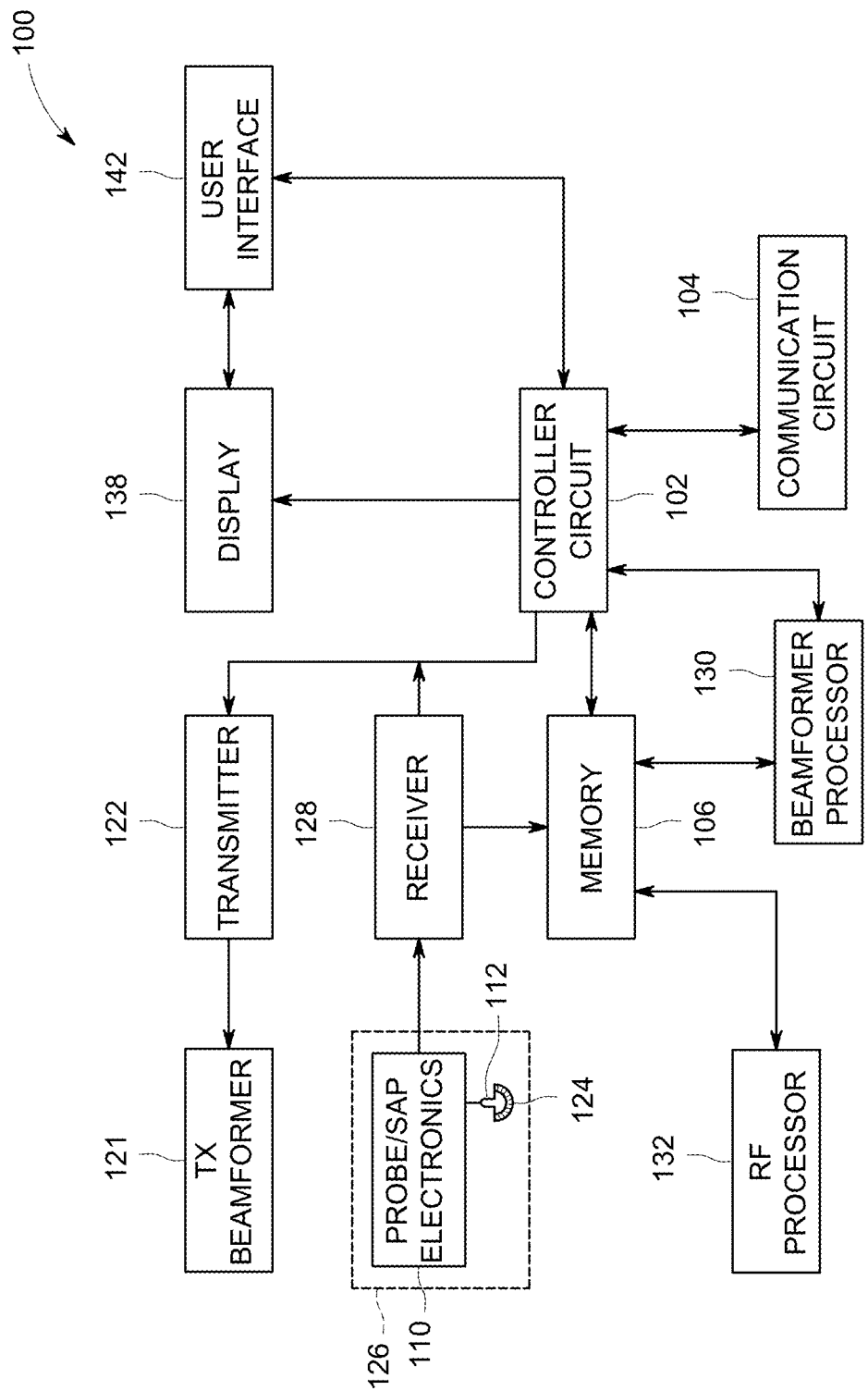
FIG. 1 illustrates a schematic block diagram of an embodiment of a medical imaging system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein generally relate to automatically determining an anatomical measurement of an ultrasound image. A medical imaging system accesses the ultrasound image, and identifies a view characteristic of an anatomical structure shown in the ultrasound image. The medical imaging system generates a diagnostic measurement (DM) tool based on the view characteristic. The DM tool has an associated set of contextual indicators. The set of contextual indicators include select contextual indicators that indicate a type of anatomical measurement. The medical imaging system receives one or more selection from the clinician. The medical imaging system identifies the type of anatomical measurement based on the one or more selections.

A technical effect of at least one embodiment described herein increases a productivity of the clinician during the ultrasound exam. A technical effect of at least one embodiment described herein enables a user to reduce errors of the anatomical measurements.

TERMS

The term "ultrasound exam" refers to an acquisition of one or more ultrasound images of one or more anatomical structures. The ultrasound exam can represent a continuous and/or discontinuous acquisition of the one or more ultrasound images (e.g., 2D, 3D, 4D) during a scan of a patient. The scan of the patient may last up to a minute and/or an hour. Optionally, the ultrasound exam can be based on one or more protocols.

The term "anatomical structure" refers to an anatomical part of a patient. Non-limiting example of an anatomical structure includes an organ (e.g., heart, kidney, lung, liver, bladder, brain, neonatal brain, embryo, abdomen, and/or the like), vascular structure (e.g., vein, artery, mitral valve, aortic valve, tricuspid valve, pulmonary valve), tissue or portion of an organ (e.g., left ventricular apex, right ventricular outflow-track, intra-ventricular septum, breast tissue, liver tissue, brain tissue, cardiac tissue, prostate tissue, and/or the like), skeletal structure, and/or the like.

The term "anatomical feature" refers to a structural feature of the anatomical structure. Non-limiting examples of anatomical features include dimensions (e.g., height, length, width, depth), a shape, a boundary dimension (e.g., thickness, shape), a number of cavities or chambers, fiducial markers, and/or the like.

The term "anatomical measurement" refers to a measurement of the anatomical feature and/or the anatomical structure shown in an ultrasound image. Non-limiting examples of the anatomical measurement may include a volume, an area, a surface area, a wall thickness (e.g., arterial inner wall, anterior wall, internal wall, posterior wall), a dimension (e.g., a depth, a diameter, a length, a width), a blood flow (e.g., velocity, peak velocity, mean velocity), valve pressure, a heart rate, a cardiac interval (e.g., R-wave to R-wave interval), a mass, a time interval, and/or the like. Optionally, the anatomical measurement is during a phase (e.g., systole, diastole) of a cardiac cycle.

The term "characteristic vector" refers to a list of one or more pixel characteristics that describe a pixel within an ultrasound image. The characteristic vector can include values for one or more of an intensity, a color, a gradient, a histogram, and/or the like of the pixel.

The term "view characteristic" for an ultrasound image refers to a view position, direction, and/or orientation of an ultrasound image as captured by an ultrasound probe. Non-limiting examples of view characteristics include a parasternal view (e.g., long axis view, short axis view), apical view (e.g., two chamber view, three chamber view, four chamber view, five chamber view), subcostal views (e.g., four chamber view, short axis view, inferior vena cava view), transvaginal coronal view, and/or the like. Ultrasound images with different view characteristics can be captured for a particular anatomical structure by adjusting the position, directional alignment and orientation of the ultrasound probe, which similarly adjusts the position, directional alignment and orientation of the field of view for the transducer(s) of the ultrasound probe. The view characteristic may include an ultrasound imaging mode (e.g., B-mode, M-mode, C-mode, Doppler) of the ultrasound image.

The term "real time" or "real-time" is used to refer to an operation, action, and/or process performed by the medical imaging system (e.g., a controller circuit) during an ultrasound exam. An ultrasound exam may include collection of multiple separate 2D or 3D ultrasound images for a common or different view windows. Optionally, the ultrasound exam may include collection of one or more cine loops of 2D or 3D ultrasound data. The operation, action or process may be performed while actively scanning a patient and/or between separate scanning operations that occur during a single ultrasound exam. A length of time associated with real time, and may vary based on a processing speed and/or operating specification (e.g., no intentional lag or delay). Real time includes updating an ultrasound image shown on the display after each ultrasound pulse within a scan and/or after each ultrasound scan sequence. Additionally or alternatively, ultrasound data may be stored temporarily in memory of the medical imaging system during the ultrasound exam and processed in a live or off-line operation.

The term "machine learning algorithm" refers to an artificial intelligence algorithm that learns from various automatic or manual inputs, such as observations and/or data. The machine learning algorithm is adjusted over multiple iterations based on the observations and/or data. For example, the machine learning algorithm is adjusted by supervised learning, unsupervised learning, and/or reinforcement learning. Non-limiting examples of machine learning algorithms are a decision tree, K-means, deep learning, artificial neural network, and/or the like.

The term "image analysis algorithm" refers to a machine learning algorithm that has been trained to perform image analysis to identify an anatomical structure, anatomical features, and/or a view characteristic of the anatomical structure of an ultrasound image.

The term "contextual indicator" refers to characteristics of an ultrasound image relative to a selection by the clinician. The contextual indicator is indicative of a type of anatomical measurement based on the selection within the ultrasound image. Non-limiting examples of the contextual indicator include a view characteristic, an anatomical feature, a position of the selection relative to the anatomical feature, an ultrasound imaging mode of the ultrasound image, a phase in a cardiac cycle at which the ultrasound image was obtained, a subsequent selection by the clinician, and/or the like.

FIG. 1 illustrates a schematic block diagram of an embodiment of a medical imaging system 100. For example, the medical imaging system 100 is shown as an ultrasound imaging system. The medical imaging system 100 may include a controller circuit 102 operably coupled to a communication circuit 104, a display 138, a user interface 142, an ultrasound probe 126, and a memory 106.

The controller circuit 102 is configured to control the operation of the medical imaging system 100. The controller circuit 102 may include one or more processors. Optionally, the controller circuit 102 may include a central processing unit (CPU), one or more microprocessors, a graphics processing unit (GPU), or any other electronic component capable of processing inputted data according to specific logical instructions. Optionally, the controller circuit 102 may include and/or represent one or more hardware circuits or circuitry that include, are connected with, or that both include and are connected with one or more processors, controllers, and/or other hardware logic-based devices. Additionally or alternatively, the controller circuit 102 may execute instructions stored on a tangible and non-transitory computer readable medium (e.g., the memory 106).

The controller circuit 102 is configured to identify one or more anatomical features in an ultrasound image. The anatomical features may represent different portions of the anatomical structure. The ultrasound image can be acquired during an ultrasound exam in real time. Optionally, the ultrasound image may be accessed by the controller circuit 102 in the memory 106 and/or received from a remote server. The anatomical features may be utilized by the controller circuit 102 to identify a view characteristic of the ultrasound image. For example, the controller circuit 102 executes an image analysis algorithm to identify the anatomical features in the ultrasound image. The controller circuit 102 identifies a position and/or orientation of the anatomical features with respect to each other in the ultrasound image. Based on the orientation of the anatomical features with respect to each other, the controller circuit 102 determines the view characteristic of the ultrasound image.

The clinician may select a first selection at a first position within the ultrasound image. The first selection is received by the controller circuit 102 from the user interface 142. For example, the clinician makes a user selection from the user interface 142. The user selection represents the first selection at the first position within the ultrasound image. The controller circuit 102 receives the first selection from the user interface 142. It may be noted, the clinician does not relate the first selection to a type of anatomical measurement. For example, the clinician does not select a type of anatomical measurement that relates to the first selection prior and/or subsequent to the first selection.

The controller circuit 102 selects a DM tool to be generated on the display 138. The DM tool is a graphical user interface (GUI). The DM tool is selected by the controller circuit 102 based on the view characteristic and/or anatomical feature proximate to the first selection. For example, DM tool has an associated set of contextual indicators 204 (FIG. 2) that correspond to different types of anatomical measurements. The set of contextual indicators 204 include select contextual indicators 204a-c indicating a type of anatomical measurement. The select contextual indicators 204a-c represent different anatomical measurements based on characteristics of an ultrasound image 202, such as the view characteristics, the anatomical feature, a position of the first selection relative to one of the anatomical features, the ultrasound imaging mode, and/or the like.

For example, the type of anatomical measurements have corresponding view characteristics. The select contextual indicator 204a, for example, may represent the anatomical measurement of a left ventricle linear dimension in end-systolic. The select contextual indicator 204a includes the view characteristic of an apical four chamber view of a heart. In another example, the select contextual indicator 204b represents the anatomical measurement of a right ventricle internal dimension in end-systolic. The select contextual indicator 204b includes the view characteristic of the apical four chamber view of the heart. In another example, the select contextual indicator 204c represents a left ventricle area in end-systolic. The select contextual indicator 204c includes the view characteristic of a left ventricle short axis epicardial view of the heart. The controller circuit 102 identifies one of the select contextual indicators 204a-c based on the view characteristic of the ultrasound image and/or the one or more selections 206-208 by the clinician.

Figure 2:
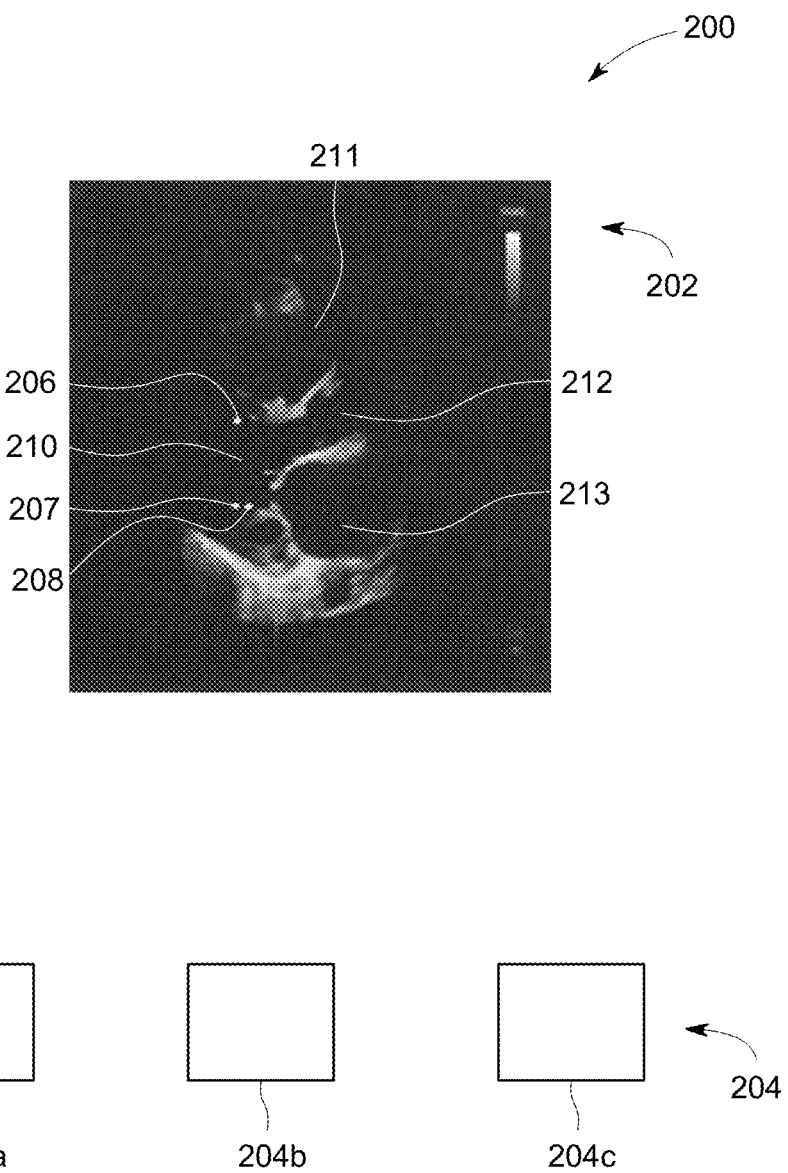
FIG. 2 illustrates an embodiment of an ultrasound image and a set of contextual indicators.

FIG. 2 illustrates an embodiment 200 of an ultrasound image 202 and the set of contextual indicators 204. The controller circuit 102 identifies anatomical features 210-213. The controller circuit 102 identifies a class and/or type of the anatomical features 210-213 of the view characteristic. For example, the anatomical feature 210 is identified as a left ventricle outflow-track, the anatomical features 211 is identified as an anterior portion of a mitral annulus, the anatomical feature 212 is identified as a right atrium, and the anatomical featured 213 is identified as a right ventricle outflow-tract. Based on the orientation and/or spatial position of the anatomical features 210-213, the controller circuit 102 identifies the view characteristic of the ultrasound image 202 as an apical four chamber view of the heart.

The clinician selects one or more selections 206-208 from the user interface 142. The controller circuit 102 receives the one or more selections 206-208 from the user interface 142. The controller circuit 102 selects one of the select contextual indicators 204a-c based on characteristics of the ultrasound image and/or the one or more selections 206-208. For example, the controller circuit 102 selects one of the select contextual indicators 204a-c based on the view characteristic, a position of the one or more selections 206-208, a phase in a cardiac cycle at which the ultrasound image was obtained, and/or the like.

The controller circuit 102 receives a selection 206 representing a position in the ultrasound image 202. The controller circuit 102 identifies the position proximate to the anatomical feature 210, which is identified as the left ventricle. The controller circuit 102 determines the position of the selection 206 relative to the anatomical feature 210. For example, the position can indicate the type of anatomical measurement. Dimensional anatomical measurements of a ventricle start at a position between a wall and pericardium. Area anatomical measurements start at a lower portion of the anatomical feature 210. The controller circuit 102 identifies the position is located between a wall and pericardium of the anatomical feature 210. Based on the position, the controller circuit 102 identifies the type of anatomical measurement corresponds to a dimensional measurement of the left ventricle. Based on the type of anatomical measurement determined from the position, the controller circuit 102 selects the select contextual indicator 204a.

Additionally or alternatively, the controller circuit 102 may identify a phase in a cardiac cycle at which the ultrasound image 202 was obtained. For example, the ultrasound image 202 was obtained during the systole phase of the cardiac cycle. The controller circuit 102 identifies the select contextual indicators 204a-c during the systole phase and relate to a dimension of the left ventricle. The controller circuit 102 identifies the left ventricle dimension measurement from the set of contextual indicators 204, which is represented as the select contextual indicator 204a.

The controller circuit 102 generates the DM tool that includes the select contextual indicator 204a on the display 138 to perform the anatomical measurement. For example, the DM tool includes calipers to measure the dimensions of the left ventricle. The controller circuit 102 positions a caliper at the position of the selection 206. The clinician selects a second selection at a second position to complete the anatomical measurement. The controller circuit 102 positions a second caliper at the second position. The controller circuit 102 automatically determines the left ventricle dimension based on a distance between the calipers.

The controller circuit 102 assigns an anatomical label indicative of the anatomical measurement. For example, the anatomical label represents the left ventricle linear dimension in end-systolic representing the select contextual indicator 204a. The controller circuit 102 overlays and/or displays the anatomical label concurrently with the ultrasound image 202, and stores a value of the anatomical measurement in the memory 106.

Optionally, the controller circuit 102 receives first and second selections 207-208. The controller circuit 102 identifies the position of the selections 207-208 proximate to the anatomical features 210-213. For example, the controller circuit 102 identifies the position of the selection 207 is proximate to the anatomical feature 210, and the controller circuit 102 identifies the position of the selection 208 is proximate to the anatomical feature 210. The controller circuit 102 determines that the first and second selections 207-208 represents the same anatomical measurement. For example, the controller circuit 102 determines the selections 207-208 are positioned proximate to the same anatomical feature 210. Since the position are proximate to the same anatomical feature 210, the controller circuit 102 determines the selections 207-208 are for the same anatomical measurement.

The controller circuit 102 identified the anatomical feature 210 as the left ventricle. The controller circuit 102 can identify the type of anatomical measurement based on the positions of the selections 207-208 relative to each other. For example, the controller circuit 102 calculates a distance between the selections 207-208. The controller circuit 102 compares the distance with a predetermined non-zero threshold stored in the memory 106. The predetermined non-zero threshold is indicative of a type of anatomical measurement. The predetermined non-zero threshold is utilized by the controller circuit 102 to determine between dimensional or area anatomical measurements. For example, when distances are less than the predetermined non-zero threshold the selections 207-208 are for the area anatomical measurement. Additionally or alternatively, when the distances are more than the predetermined non-zero threshold the selections 207-208 are for the dimensional anatomical measurement.

The controller circuit 102 determines the distance is less than the predetermined non-zero threshold, and for an area anatomical measurement. The controller circuit 102 identifies the select contextual indicators 204a-c relate to an area of the left ventricle. The controller circuit 102 identifies the left ventricle area in end-systolic from the set of contextual indicators 204, which is represented as the select contextual indicator 204c. The controller circuit 102 generates the DM tool that includes the select contextual indicator 204c on the display 138 to perform the anatomical measurement. For example, the DM tool includes an area-trace tool to measure the area of the left ventricle. Optionally, the area-trace tool may represent overlaying a shape on the anatomical feature 210. For example, the controller circuit 102 overlays an elliptical shape on the anatomical feature 210. The clinician can adjust a shape (e.g., axes, dimensions) of the elliptical shape based on selections from the user interface 142. The controller circuit 102 automatically determines the area of the elliptical shape to corresponding to the select contextual indicator 204c. The controller circuit 102 assigns an anatomical label indicative of the anatomical measurement. For example, the anatomical label represents the area of the left ventricle are in end-systolic. The controller circuit 102 overlays and/or displays the anatomical label concurrently with the ultrasound image 202, and stores a value of the anatomical measurement in the memory 106. Additionally or alternatively, the area-trace tool may be based on different shapes (e.g., circular shape), linear area (e.g., rectangular shape), free form (e.g., tracing a non-linear trace or form based on a plurality of selections by the clinician).

The controller circuit 102 (FIG. 1) may be operably coupled to and/or control a communication circuit 104. The communication circuit 104 is configured to receive and/or transmit information with one or more alternative medical imaging systems, the remote server, and/or the like along a uni-directional and/or bi-directional communication link. The remote server may represent a database that includes patient information, machine learning algorithms, remotely stored ultrasound images of a patient, and/or the like. The communication circuit 104 may represent hardware that is used to transmit and/or receive data along the uni-directional and/or bi-directional communication link. The communication circuit 104 may include a transceiver, receiver, transceiver and/or the like and associated circuitry (e.g., antennas) for wired and/or wirelessly communicating (e.g., transmitting and/or receiving) with the one or more alternative medical imaging systems, the remote server, and/or the like. For example, protocol firmware for transmitting and/or receiving data along the uni-directional and/or bi-directional communication link may be stored in the memory 106, which is accessed by the controller circuit 102. The protocol firmware provides the network protocol syntax for the controller circuit 102 to assemble data packets, establish and/or partition data received along the bi-directional communication links, and/or the like.

The uni-directional and/or bi-directional communication links may be a wired (e.g., via a physical conductor) and/or wireless communication (e.g., utilizing radio frequency (RF)) link for exchanging data (e.g., data packets) between the one or more alternative medical imaging systems, the remote server, and/or the like. The bi-directional communication links may be based on a customized communication protocol and/or a standard communication protocol, such as Ethernet, TCP/IP, Wi-Fi, 802.11, Bluetooth, and/or the like.

The controller circuit 102 is operably coupled to the display 138 and the user interface 142. The display 138 may include one or more liquid crystal displays (e.g., light emitting diode (LED) backlight), organic light emitting diode (OLED) displays, plasma displays, CRT displays, and/or the like. The display 138 may display patient information, one or more ultrasound images and/or videos, components of a graphical user interface, one or more 2D, 3D, or 4D ultrasound image data sets from ultrasound data stored in the memory 106 or currently being acquired in real-time, anatomical measurements, diagnosis, treatment information, tags, and/or the like received by the display 138 from the controller circuit 102.

The user interface 142 controls operations of the controller circuit 102 and the medical imaging system 100. The user interface 142 is configured to receive inputs from the clinician and/or operator of the medical imaging system 100. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller circuit 102, which is shown on the display 138. The touch screen display can detect a presence of a touch from the operator on the display 138 and can also identify a location of the touch with respect to a surface area of the display 138. For example, the user may select one or more user interface components of the GUI shown on the display by touching or making contact with the display 138. The user interface components may correspond to graphical icons, textual boxes, menu bars, and/or the like shown on the display 138. The user interface components may be selected, manipulated, utilized, interacted with, and/or the like by the clinician to instruct the controller circuit 102 to perform one or more operations as described herein. The touch may be applied by, for example, at least one of an individual's hand, glove, stylus, and/or the like.

The memory 106 includes parameters, algorithms, protocols of one or more ultrasound exams, data values, and/or the like utilized by the controller circuit 102 to perform one or more operations described herein. The memory 106 may be a tangible and non-transitory computer readable medium such as flash memory, RAM, ROM, EEPROM, and/or the like.

The memory 106 may include an image analysis algorithm. The controller circuit 102 executes the image analysis algorithm to identify the one or more anatomical features and/or the view characteristic of the ultrasound image. Optionally, the image analysis algorithm may be received along the uni-directional or bi-directional communication links via the communication circuit 104 and stored in the memory 106.

The image analysis algorithm may be defined by one or more machine learning algorithms to identify the view characteristic in the ultrasound image based on the one or more anatomical features. The image analysis algorithm may be executed by the controller circuit 102 as the ultrasound images are being acquired (e.g., in real-time) by the medical imaging system 100. Additionally or alternatively, the image analysis algorithm may be executed by the controller circuit 102 as the ultrasound images are loaded by the clinician from the memory 106 and/or the remote server.

Optionally, the image analysis algorithm utilizes a pixel and/or voxel analysis of the ultrasound image. For example, the anatomical features are identified by the controller circuit 102 based on characteristics of the pixels and/or voxels in the ultrasound image. The controller circuit 102 defines characteristic vectors for the pixels and/or voxels. The characteristic vector may represent an array of information that describes the pixels and/or voxels. The characteristic vector includes a histogram, gradients, a color, an intensity or brightness, and/or the like of the pixels and/or voxels. Optionally, the image analysis algorithm may correspond to an artificial neural network formed by the controller circuit 102 and/or the remote server. The image analysis algorithm may be divided into a plurality of artificial neural layers. The artificial neural layers may represent different functions and/or outputs of the image analysis algorithm. For example, the artificial neural layers include an input layer configured to receive an input image, an output layer configured to identify the anatomical structure of the input image, a view characteristic layer, and/or one or more intermediate layers. The artificial neural layers represent different groups or sets of artificial neurons, which can represent different functions performed by the controller circuit 102 on the ultrasound image. The artificial neurons in the layers are configured to examine individual pixels in the ultrasound image. For example, the artificial neurons may define the characteristic vectors for the ultrasound image.

The artificial neurons further may apply different weights in the functions applied to the ultrasound image to attempt to identify the anatomical structure. The image analysis algorithm identifies the anatomical structure by assigning or associating different pixels in the ultrasound image with different anatomical features based on the characteristic vectors. For example, the characteristics vectors are utilized by the controller circuit 102 to determine scores for the pixels. The scores can indicate the probability that the pixel represents a particular anatomical feature.

Additionally or alternatively, the image analysis algorithm uses a classification algorithm to identify the anatomical features. For example, the classification algorithm identifies one or more anatomical features in the ultrasound image. The identification of the one or more anatomical features can be based on a size, a shape, and/or the like. The classification algorithm classifies (e.g., random forest classifier, principal component analysis, and/or that like) the one or more anatomical features into a plurality of types or classes. The types or classes represent different anatomical features of the anatomical structure.

The controller circuit 102 may determine the view characteristic of the anatomical structure based on the one or more anatomical features. For example, controller circuit 102 identifies an orientation and/or spatial position of the one or more anatomical features within the ultrasound image. The controller circuit 102 determines the view characteristic based on the orientation and/or spatial position of the one or more anatomical features with respect to each other. The spatial position may include a distance(s) and/or relation between at least two of the anatomical features. Change in the spacing between at least two anatomical features may occur when the anatomical structure is not perpendicular to the view characteristic of the transducer array 112.

Additionally or alternatively, the image analysis algorithm is configured to identify one or more of the anatomical features independent of the ultrasound imaging mode. For example, the image analysis algorithm is configured to identify one or more of the anatomical features of a Doppler flow ultrasound image, a B-mode ultrasound image, a C-mode ultrasound image, an M-mode ultrasound image, and/or the like.

The ultrasound probe 126 may have a transmitter 122, transmit beamformer 121 and probe/SAP electronics 110. The probe/SAP electronics 110 may be used to control the switching of the transducer elements 124. The probe/SAP electronics 110 may also be used to group transducer elements 124 into one or more sub-apertures. The ultrasound probe 126 may be configured to acquire ultrasound data or information from the anatomical structure of the patient. The ultrasound probe 126 is communicatively coupled to the controller circuit 102 via the transmitter 122. The transmitter 122 transmits a signal to a transmit beamformer 121 based on acquisition settings received by the controller circuit 102. The acquisition settings may define an amplitude, pulse width, frequency, gain setting, scan angle, power, time gain compensation (TGC), resolution, and/or the like of the ultrasonic pulses emitted by the transducer elements 124. The transducer elements 124 emit pulsed ultrasonic signals into the patient (e.g., a body). The acquisition settings may be defined by the user operating the user interface 142. The signal transmitted by the transmitter 122 in turn drives a plurality of transducer elements 124 within a transducer array 112.

The transducer elements 124 emit pulsed ultrasonic signals into a body (e.g., patient) or volume corresponding to the acquisition settings along one or more scan planes. The ultrasonic signals may include, for example, one or more reference pulses, imaging pulses, one or more pushing pulses (e.g., shear-waves), and/or one or more pulsed wave Doppler pulses. At least a portion of the pulsed ultrasonic signals backscatter from the anatomical structure to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the anatomic structure, differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals, which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves received by each transducer element 124 at various times. After digitization, the signals still may preserve the amplitude, frequency, phase information of the backscatter waves.

Optionally, the controller circuit 102 may retrieve the digitized signals stored in the memory 106 to prepare for the beamformer processor 130. For example, the controller circuit 102 may convert the digitized signals to baseband signals or compressing the digitized signals.

The beamformer processor 130 may include one or more processors. Optionally, the beamformer processor 130 may include a central processing unit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or a part of the controller circuit 102. For example, the operations described as being performed by the beamformer processor 130 may be configured to be performed by the controller circuit 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central processing unit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or a part of the controller circuit 102. For example, the operations described as being performed by the RF processor 132 may be configured to be performed by the controller circuit 102.

The RF processor 132 may generate different ultrasound image data types and/or modes (e.g., B-mode, C-mode, M-mode, color Doppler (e.g., color flow, velocity/power/variance), tissue Doppler, and Doppler energy) for multiple scan planes or different scanning patterns based on the predetermined settings of the first model. For example, the RF processor 132 may generate tissue Doppler data for multi-scan planes. The RF processor 132 gathers the information (e.g., I/Q, B-mode, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller circuit 102.

The controller circuit 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller circuit 102 during the ultrasound exam as the echo signals are received. Additionally or alternatively, the ultrasound data may be stored temporarily in the memory 106 during the ultrasound exam and processed in less than real-time in a live or off-line operation.

The memory 106 may be used for storing processed frames of acquired ultrasound data that are not scheduled to be displayed immediately or to store post-processed images, firmware or software corresponding to, for example, a graphical user interface, one or more default image display settings, programmed instructions, and/or the like. The memory 106 may store the ultrasound images such as 3D ultrasound image data sets of the ultrasound data, where such 3D ultrasound image data sets are accessed to present 2D and 3D images. For example, a 3D ultrasound image data set may be mapped into the corresponding memory 106, as well as one or more reference planes. The processing of the ultrasound data, including the ultrasound image data sets, may be based in part on user inputs, for example, user selections received at the user interface 142.

Figure 3:
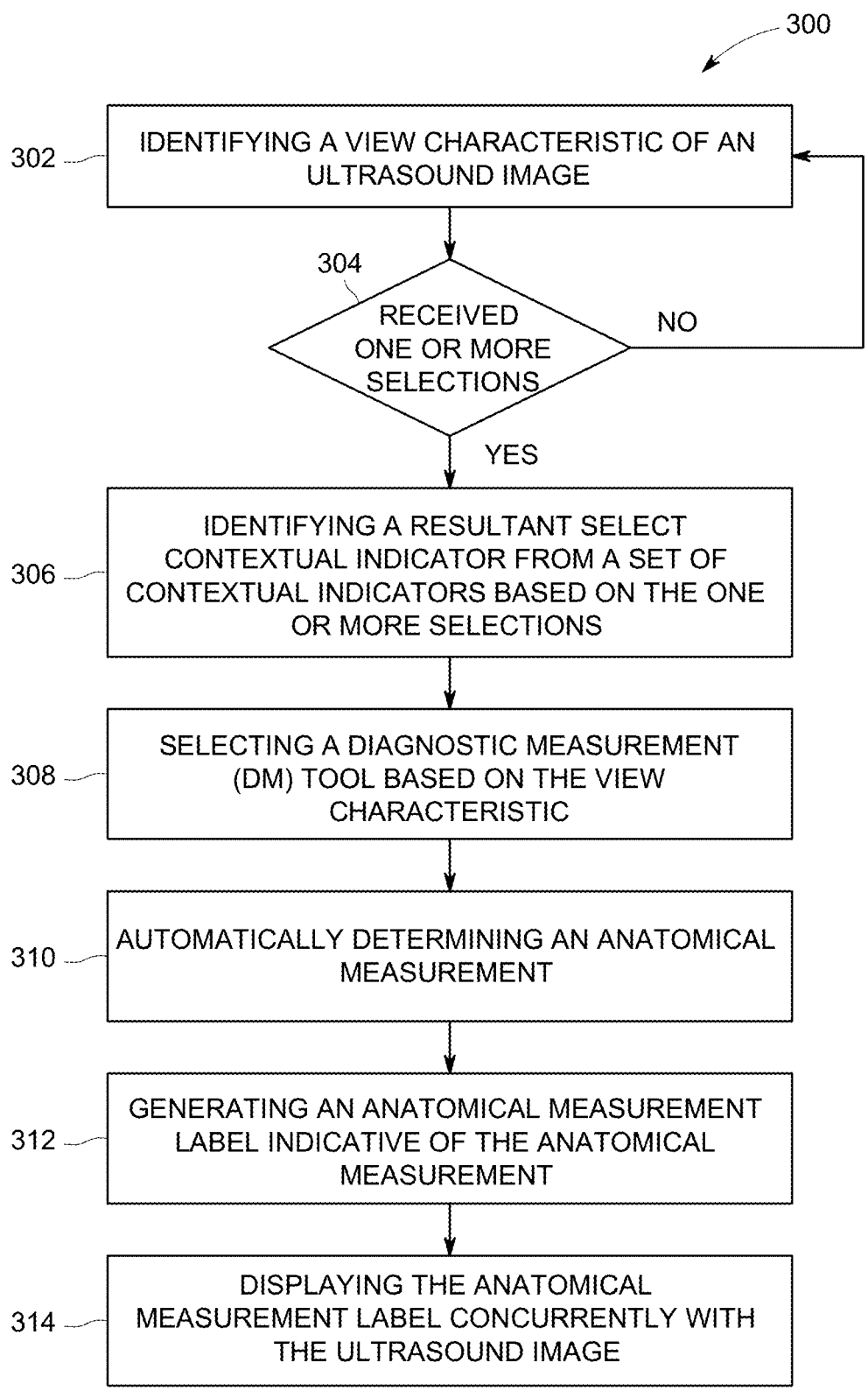
FIG. 3 illustrates a flow chart of an embodiment of a method for automatically determine an anatomical measurement.

FIG. 3 illustrates a flow chart of a method 300 for automatically determining an anatomical measurement, in accordance with an embodiment herein. The method 300, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It may be noted that the steps described of the method 300 may be performed during the ultrasound exam in real-time. In various embodiments, portions, aspects, and/or variations of the method 300 may be used as one or more algorithms to direct hardware to perform one or more operations described herein.

Figure 4:
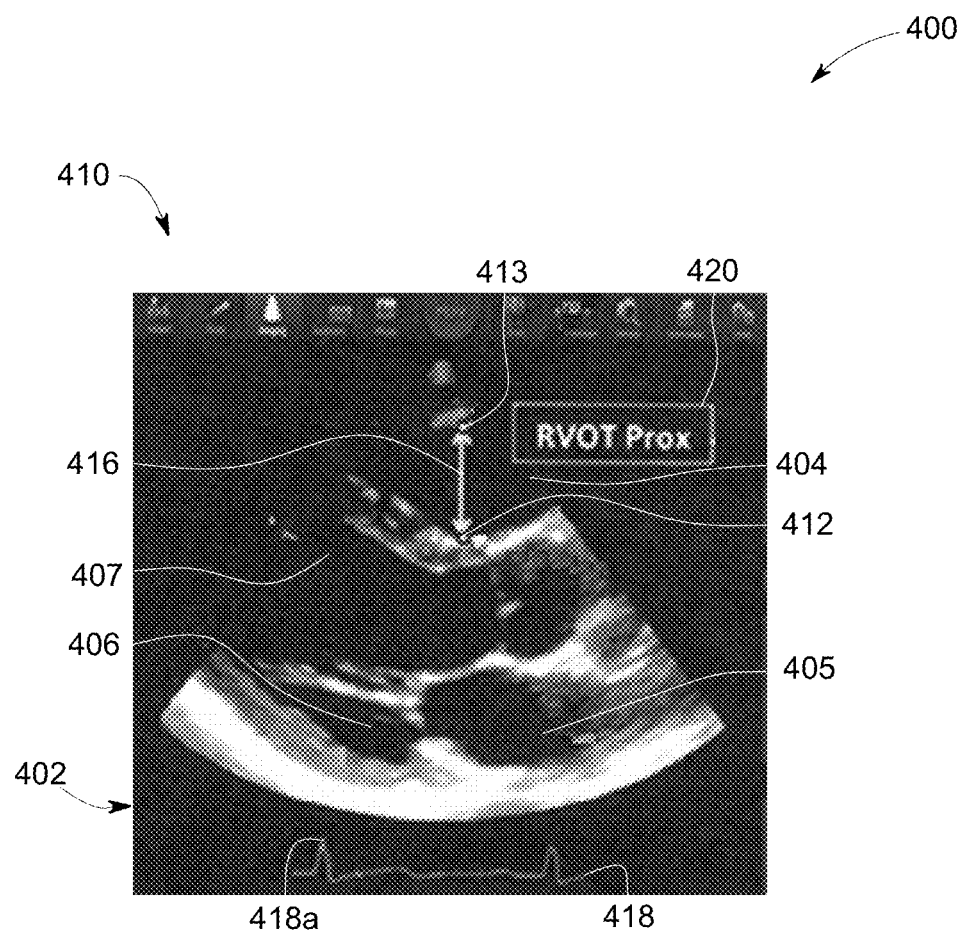
FIG. 4 illustrates an embodiment of a diagnostic measurement tool for an ultrasound image.

Beginning at 302, the controller circuit 102 identifies a view characteristic of an ultrasound image 402. FIG. 4 illustrates a DM tool 400 for the ultrasound image 402. The DM tool 400 includes a plurality of user interface components 410. The clinician can select one or more of the user interface components 410 to adjust operations of the medical imaging system 100. For example, the controller circuit 102 can adjust ultrasound signals transmitted by the ultrasound probe 126, selection of different ultrasound imaging modes, and/or the like based on selections of the user interface components 410.

The ultrasound image 402 is based on ultrasound data received from the ultrasound probe 126. The ultrasound probe 126 acquires ultrasound data of the anatomical structure within the patient. During the ultrasound exam of the patient, the ultrasound probe 126 may emit ultrasound signals from the transducer array 112 at a set rate within the patient. At least a portion of the ultrasound signals are backscattered from the anatomical structure of interest and received by the ultrasound probe 126 via the receiver 128 as ultrasound data. The controller circuit 102 is configured to generate the ultrasound image 402 of the anatomical structure based on the ultrasound data. Additionally or alternatively, the clinician may select the ultrasound image 402 stored in the memory 106. For example, a plurality of ultrasound images were acquired during the ultrasound exam. The clinician can select one of the plurality of ultrasound images for the ultrasound image 402 using the user interface 142. For example, the controller circuit 102 receives a user selection from the user interface 142 selecting the ultrasound image 402.

The controller circuit 102 analyzes the ultrasound image 402 to identify the one or more anatomical features 404-407. For example, the controller circuit 102 executes the image analysis algorithm stored in the memory 106. The controller circuit 102 identifies types and/or classes of the anatomical features 404-407. For example, the controller circuit 102 determines a first set of characteristic vectors for the ultrasound images 402. The controller circuit 102 determines probabilities for the first set of characteristic vectors. The probabilities representing an identity of the first anatomical feature 404. The controller circuit 102 identifies the anatomical feature 404 as the right ventricle. For example, the controller circuit 102 identifies the anatomical feature 404 has a higher probability of being the right ventricle relative to the remaining probabilities. Optionally, the controller circuit 102 may identify the anatomical features 404-407 of the ultrasound image 402 concurrently and/or simultaneously.

The controller circuit 102 determines the view characteristic of the ultrasound image 402 based on the one or more anatomical features 404-407. The controller circuit 102 determines the view characteristic based on the orientation and/or spatial position of the anatomical features 404-407 of the ultrasound image 402. For example, the controller circuit 102 analyzes the position and/or orientation of the anatomical features 404-407 to determine the view characteristic of the ultrasound image 402 (e.g., a left ventricle outflow-tract, a left atrium, a right ventricle outflow-tract, a right atrium, an anterior portion of a mitral annulus). For example, based on the orientation and/or spatial position of the anatomical features 404-407, the controller circuit 102 determines the characteristic view is a parasternal long axis view of the heart.

At 304, the controller circuit 102 determines that one or more selections 412-413 are received. The one or more selections 412-413 are indicative of the anatomical measurement performed by the clinician on the ultrasound image 402. The one or more selections 412-413 are positioned differently within the ultrasound image 402. The one or more selections 412-413 are received by the controller circuit 102 from the user interface 142. For example, the clinician may select a first position in the ultrasound image 402 using the user interface 142. The first position is represented as a graphical icon representing the selection 413. Optionally, the controller circuit 102 may receive more than the two selections 412-413 shown in FIG. 4.

At 306, the controller circuit 102 identifies a resultant select contextual indicator from sets of contextual indicators. The resultant select contextual indicator represents the type of anatomical measurement performed by the clinician. The controller circuit 102 analyzes the ultrasound image 402 and/or the first position to identify the resultant select contextual indicator. Different sets of contextual indicators are included in the plurality of DM tools stored in the memory 106. The controller circuit 102 analyzes the sets of contextual indicators, and identifies the resultant select contextual indicator that represents the anatomical measurement performed by the clinician.

For example, the controller circuit 102 can narrow the plurality of DM tools to a set of DM tools based on the view characteristic. The sets of contextual indicators include select contextual indicators corresponding to different view characteristics. For example, a first DM tool can include a set of contextual indicators for anatomical structures relating to a view characteristic of a skeletal structure. The set of contextual indicators can include anatomical measurements that measure a length of a bone, a diameter of a bone, and/or the like. In another example, a second DM tool can include a set of contextual indicators for anatomical structures relating to a view characteristic of a fetal brain. The set of contextual indictors can include select contextual indicators to measure dimensions of the fetal brain, dimensions of the skull, and/or the like.

Additionally or alternatively, a portion of the contextual indicators may have a common view characteristic. For example, a first and second DM tool may include anatomical measurements of anatomical features of an apical five chamber view of the heart. The first and second DM tools may include different sets of contextual indicators for different phases of the cardiac cycle. For example, the first DM tool may include select contextual indicators for measuring ventricle dimensions during the diastole phase, and the second DM tool may include select contextual indicators for measuring ventricle dimensions during the systole phase.

The controller circuit 102 identifies the select contextual indicators representing types of anatomical measurements for a parasternal long axis view of the heart (e.g., the view characteristic of the ultrasound image 402). For example, the controller circuit 102 analyzes the sets of contextual indicators of the plurality of DM tools. The controller circuit 102 identifies the select contextual indicators that have anatomical measurements for a parasternal long axis view of the heart. The DM tools identified by the controller circuit 102 that have the identified select contextual indicators are included in the set of DM tools.

The controller circuit 102 identifies the resultant select contextual indicator from the set of DM tools based on the type of anatomical measurement being performed by the clinician. The controller circuit 102 can identify the resultant select contextual indicator based on the anatomical features 404-407 proximate to the first position. The controller circuit 102 identified the first position is proximate to the anatomical feature 404, which was identified as the right ventricle. The controller circuit 102 analyzes the select contextual indicators of the set of DM tools to identify candidate DM tools that include anatomical measurements of the right ventricle. Optionally, the type of anatomical measurement can be determined by the controller circuit 102 based on the first position relative to the anatomical feature 404. For example, dimensional anatomical measurements start between a wall and pericardium of the right ventricle. In another example, area anatomical measurements start at a lower portion of the anatomical feature 404. The controller circuit 102 identifies the first position is located at an upper portion between a wall and pericardium of the anatomical feature 404. Based on the position, the controller circuit 102 identifies the type of anatomical measurement is a dimensional anatomical measurement. The controller circuit 102 identifies the resultant select contextual indicator from the candidate DM tools that represents the dimensional anatomical measurement of the right ventricle.

Additionally or alternatively, the controller circuit 102 may identify the type of anatomical measurement based on the phase in the cardiac cycle at which the ultrasound image 402 was obtained. The ultrasound image 402 includes a cardiac cycle waveform 418. The cardiac cycle waveform 418 includes an indicator 418a. The indicator 418a is indicative on when along the cardiac cycle waveform 418 the ultrasound image 402 was obtained. For example, the indicator 418a indicates the ultrasound image 402 was obtained during the systole phase of the cardiac cycle. The controller circuit 102 analyzes the select contextual indicators of the set of DM tools to identify the candidate DM tools that include anatomical measurements during the systole phase. Optionally, the controller circuit 102 can further utilize the first position to identify the candidate DM tools. For example, the controller circuit 102 can identify select contextual indicators that are during the systole phase of the right ventricle.

Additionally or alternatively, the controller circuit 102 may identify the type of anatomical measurement based on the view characteristic. The view characteristic includes the ultrasound imaging mode of the ultrasound image 402. The type of the ultrasound imaging mode is used by the controller circuit 102 to identify different types of anatomical measurements. For example, ultrasound images acquired in the ultrasound imaging mode of Doppler and/or color flow are used for anatomical measurements related to blood flow. Non-limiting examples of anatomical measurements relating to blood flow include a velocity, pressure, heart rate, and/or the like. For view characteristics that include the Doppler and/or color flow modes, the controller circuit 102 may identify the select contextual indicators that are anatomical measurements related to blood flow.

In another example, ultrasound images acquired in the ultrasound imaging mode of M-mode are used for anatomical measurements related to depth, intervals, and/or the like. Non-limiting examples of anatomical measurements relating to M-mode include a wall thickness, internal dimension, septal thickness, root diameter, R-wave to R-wave interval, cusp separation, septal separation, valve excursion, diastolic function (e.g., D-to-E, E-to-F), and/or the like. For view characteristics that include the M-mode, the controller circuit 102 may identify the select contextual indicators that are anatomical measurements related to the M-mode.

In another example, ultrasound images acquired in the ultrasound imaging mode of B-mode, C-mode, and/or the like are used for dimensional measurements related to volume, mass, area, shunts, and/or the like. Optionally, the dimensional measurements occur at different phases (e.g., systole, diastole) of the cardiac cycle. Non-limiting examples of anatomical measurements relating to dimensional measurements include an area, mass, anterior wall thickness, internal dimension, septal thickness, septal thickness, outflow tact diameter, artery diameter, valve diameter, pulmonic diameter, systemic diameter, and/or the like. For view characteristics that include the B-mode, C-mode and/or the like, the controller circuit 102 may identify the select contextual indicators that are anatomical measurements related to dimensional measurements.

The view characteristic of the ultrasound image 402 was obtained in the B-mode. The controller circuit 102 analyzes the select contextual indicators of the set of DM tools to identify the candidate DM tools that include dimensional measurements. Optionally, the controller circuit 102 can further utilize the first position to identify the candidate DM tools for a particular anatomical feature. For example, the controller circuit 102 can identify select contextual indicators that are dimensional measurements of the right ventricle (e.g., the anatomical feature 404).

Additionally or alternatively, the controller circuit 102 may compare the one or more selections 412-413 to identify the resultant select contextual indicator from the sets of contextual indicators. For example, the selection 412 may be received by the controller circuit 102 subsequent to the selection 413. The controller circuit 102 calculates a distance between the positions of the selections 412-413. The distance between the selections 412-413 is indicative of a length anatomical measurement or an area anatomical measurement. For example, the controller circuit 102 compares the distance with the predetermined non-zero threshold stored in the memory 106. The predetermined non-zero threshold is indicative of a type of anatomical measurement. The predetermined non-zero threshold is utilized by the controller circuit 102 to determine between dimensional or area anatomical measurements.

For example, when distances are less than the predetermined non-zero threshold the selections 412-413 are for the area anatomical measurement. The area anatomical measurement may represent a non-linear trace of the anatomical features 404. For example, the selections 412-413 represent the clinician tracing a boarder of the anatomical feature 404, overlaying a shape, and/or the like. Based on the distance between the selections 412-413 and the proximity to the anatomical feature 404, the controller circuit 102 determines the resultant contextual indicator is indicative of the area anatomical measurement of the anatomical feature 404.

Additionally or alternatively, when the distances are more than the predetermined non-zero threshold, as shown in FIG. 4, the selections 412-413 represent the dimensional anatomical measurement (e.g., length) of the anatomical feature 404.

At 308, the controller circuit 102 selects a select DM tool based on the view characteristic. For example, the controller circuit 102 identifies the select DM tool (e.g., the DM tool 400) having the resultant contextual indicator for a right ventricular outflow tract diameter. The controller circuit 102 generates the select DM tool on the GUI for the display 138.

At 310, the controller circuit 102 automatically determines an anatomical measurement 416. The anatomical measurement 416 is performed utilizing the DM tool 400. The DM tool 400 can include measurement tools. The measurement tools can be graphical icons overlaid on the ultrasound image 402. Non-limiting examples of measurement tools include calipers (e.g., depth calipers, slope calipers, dimensional calipers, time calipers), traces (e.g., boundary trace, non-linear area trace, velocity trace), area shapes (e.g., ellipse tool, circular tool), points (e.g., velocity points), and/or the like. The measurement tools enable the controller circuit 102 to determine the anatomical measurement.

For example, the DM tool 400 includes measurement tools to measure the right ventricular outflow tract diameter. The measurement tools are calipers. The controller circuit 102 positions a first caliper at the first position (e.g., the selection 413) received at 304. The clinician may select a second position at the selection 412. For example, the clinician selects the selection 412 using the user interface 142. The controller circuit 102 receives the selection 412 from the user interface 142, and position a second caliper at the second position. Additionally or alternatively, the selections 412-413 were received concurrently at 304. The controller circuit 102 positions the first and second calipers at the first and second positions. The controller circuit 102 automatically determines a distance between the first and second calipers. The distance represents the right ventricular outflow tract diameter (e.g., the anatomical measurement 416).

At 312, the controller circuit 102 generates an anatomical measurement label 420 indicative of the anatomical measurement 416. The anatomical measurement label 420 can include textual information, numerical information, and/or the like representing the anatomical measurement 416.

At 314, the controller circuit 102 displays the anatomical measurement label concurrently with the ultrasound image 402. For example, the controller circuit 102 overlays the anatomical measurement label 420 on the ultrasound image 402 to be shown concurrently on the display 138. Optionally, the controller circuit 102 adds metadata to the ultrasound image 402 store in the memory 106. The metadata is indicative of the anatomical measurement label 420.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A computer implemented method, comprising:
identifying a view characteristic of an ultrasound image, wherein the ultrasound image includes one or more anatomical features;
receiving a first selection at a first position within the ultrasound image;
automatically identifying a select contextual indicator based on the view characteristic and the first position;
selecting a diagnostic measurement (DM) tool based on the select contextual indicator which is generated on a display;
automatically determining an anatomical measurement, to be performed upon the ultrasound image utilizing the DM tool, based on the select contextual indicator and wherein the contextual indicator corresponds to one or more characteristics of an ultrasound image relative to the first selection.

2. The computer implemented method of claim 1, wherein the DM tool has an associated set of contextual indicators that correspond to different types of anatomical measurements, the determining operation including identifying a select contextual indicator indicating a type of anatomical measurement to be obtained from the first selection.

3. The computer implemented method of claim 2, wherein the select contextual indicator includes at least one of i) a first anatomical feature proximate to the first position, ii) the view characteristic, or iii) a phase in a cardiac cycle at which the ultrasound image was obtained.

4. The computer implemented method of claim 1, further comprising receiving a second selection at a second position within the ultrasound image subsequent to the first selection, the select contextual indicator automatically identified based, in part, on a relation between the first and second selections.

5. The computer implemented method of claim 4, further comprising calculating a distance between the first and second positions, wherein the distance is indicative of a length anatomical measurement or an area anatomical measurement, wherein the area anatomical measurement is indicative of a non-linear trace.

6. The computer implemented method of claim 4, further comprising identifying a first anatomical feature proximate to the first position and a second anatomical feature proximate to the second position, wherein the determining operation identifies the anatomical measurement when the first and second anatomical features are the same.

7. The computer implemented method of claim 1, wherein the determining operation includes identifying the first position relative to the first anatomical feature.

8. The computer implemented method of claim 1, further comprising selecting the DM tool from a set of DM tools based on the first position.

9. The computer implemented method of claim 1, further comprising generating an anatomical measurement label indicative of the anatomical measurement, and displaying the anatomical measurement label concurrently with the ultrasound image on a display.

10. The computer implemented method of claim 1, wherein the view characteristic comprises a characteristic vector that represents an array of information that describes at least one of a group of pixels or a group of voxels.

11. A medical imaging system comprising:
an ultrasound probe configured to acquire ultrasound data of an anatomical structure;
a display; and
a controller circuit configured to:
identify a view characteristic of an ultrasound image, wherein the ultrasound image includes one or more anatomical features;
receive a first selection at a first position within the ultrasound image;
automatically identify a select contextual indicator based on the view characteristic and the first position;
select a diagnostic measurement (DM) tool based on the select contextual indicator which is generated on the display;
automatically determine an anatomical measurement, to be performed upon the ultrasound image utilizing the DM tool, based on the select contextual indicator and wherein the contextual indicator corresponds to one or more characteristics of an ultrasound image relative to the first selection.

12. The medical imaging system of claim 11, wherein the DM tool has an associated set of contextual indicators that correspond to different types of anatomical measurements, the determining operation including identifying a select contextual indicator indicating a type of anatomical measurement to be obtained from the first selection.

13. The medical imaging system of claim 12, wherein the select contextual indicator includes at least one of i) a first anatomical feature proximate to the first position, ii) the view characteristic, or iii) a phase in a cardiac cycle at which the ultrasound image was obtained.

14. The medical imaging system of claim 11, wherein the controller circuit is configured to receive a second selection at a second position within the ultrasound image subsequent to the first selection.

15. The medical imaging system of claim 14, wherein the controller circuit is configured to calculate a distance between the first and second positions, wherein the distance is indicative of a length anatomical measurement or an area anatomical measurement, wherein the area anatomical measurement is indicative of a non-linear trace.

16. The medical imaging system of claim 14, wherein the controller circuit is configured to identify a first anatomical feature proximate to the first position and a second anatomical feature proximate to the second position, wherein the controller circuit is configured to identify the anatomical measurement when the first and second anatomical features are the same.

17. The medical imaging system of claim 11, wherein the controller circuit is configured to identify the first position relative to the first anatomical feature.

18. The medical imaging system of claim 11, wherein the controller circuit is configured to select the DM tool from a set of DM tools based on the first position.

19. The medical imaging system of claim 11, wherein the controller circuit is configured to generate an anatomical measurement label indicative of the anatomical measurement, and display the anatomical measurement label concurrently with the ultrasound image on a display.

20. The medical imaging system of claim 11, wherein the view characteristic comprises a characteristic vector that represents an array of information that describes at least one of a group of pixels or a group of voxels.

21. A computer implemented method, comprising:
    identifying a view characteristic of an ultrasound image, wherein the ultrasound imaging includes one or more anatomical features;
    receiving a first selection at a first position within the ultrasound image and a second selection at a second position within the ultrasound image;
    automatically identifying a select contextual indicator based on the view characteristic, the first position and the second position;
    selecting a diagnostic measurement (DM) tool based on the select contextual indicator wherein the DM tool has an associated set of contextual indicators that correspond to different types of anatomical measurements;
    identifying a select contextual indicator indicating a type of anatomical measurement to be obtained from the first and second selections;
    automatically determining an anatomical measurement, to be performed upon the ultrasound image utilizing the DM tool, based on the select contextual indicator and wherein the contextual indicator corresponds to one or more characteristics of an ultrasound image relative to the first selection.

22. The computer implemented method of claim 21, wherein the select contextual indicator includes at least one of i) a distance between the first and second positions, ii) a first anatomical feature proximate to the first position, iii) a second anatomical feature proximate to the second position, or iv) a phase in a cardiac cycle at which the ultrasound image was obtained.

* * * * *